(12) United States Patent
Laiosa

(10) Patent No.: US 8,308,695 B2
(45) Date of Patent: Nov. 13, 2012

(54) AUTOMATIC INJECTION DEVICE WITH ACTIVELY TRIGGERED SYRINGE WITHDRAWAL

(75) Inventor: John Laiosa, Lodi, NJ (US)

(73) Assignee: SHL Group AB, Nacka Strand (SE)

( * ) Notice: Subject to any disclaimer, the term of this patent is extended or adjusted under 35 U.S.C. 154(b) by 286 days.

(21) Appl. No.: 12/742,870

(22) PCT Filed: Nov. 14, 2008

(86) PCT No.: PCT/EP2008/065512
§ 371 (c)(1),
(2), (4) Date: Aug. 2, 2010

(87) PCT Pub. No.: WO2009/063030
PCT Pub. Date: May 22, 2009

(65) Prior Publication Data
US 2010/0298780 A1    Nov. 25, 2010

Related U.S. Application Data

(60) Provisional application No. 60/987,862, filed on Nov. 14, 2007.

(51) Int. Cl.
*A61M 5/32* (2006.01)
*A61M 5/20* (2006.01)

(52) U.S. Cl. .......... 604/198; 604/137; 604/157
(58) Field of Classification Search .......... 604/110, 604/131, 134–139, 156, 157, 192, 195–198
See application file for complete search history.

(56) References Cited

FOREIGN PATENT DOCUMENTS
EP      1743666 A1  *  1/2007
* cited by examiner

*Primary Examiner* — Nicholas Lucchesi
*Assistant Examiner* — Nathan R Price
(74) *Attorney, Agent, or Firm* — Potomac Patent Group PLLC

(57) ABSTRACT

The present invention relates to an injection device, comprising a housing (10) including a container carrier (16) having a medicament container (18) and a needle (22) attached to the medicament container, a needle shield (12), means for initiating a penetration; penetration means for automatic penetration of needle, means for automatically injecting medicament, means for an automatically withdrawing the needle. The invention is characterized in an active triggering withdrawal mechanism capable of allowing the means for automatically withdrawing the needle to be triggered when the injection device starts to be removed from an injection site.

5 Claims, 16 Drawing Sheets

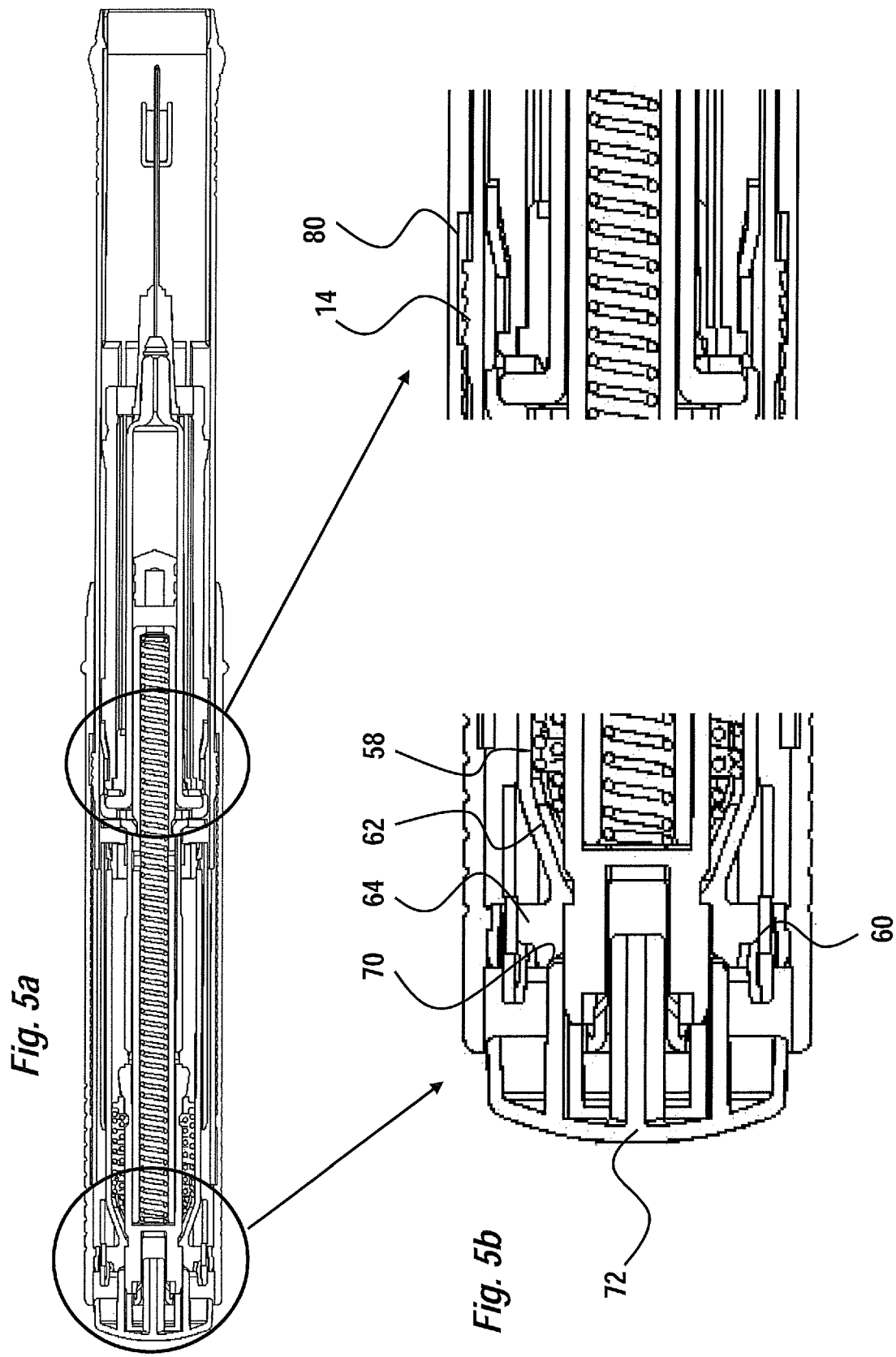

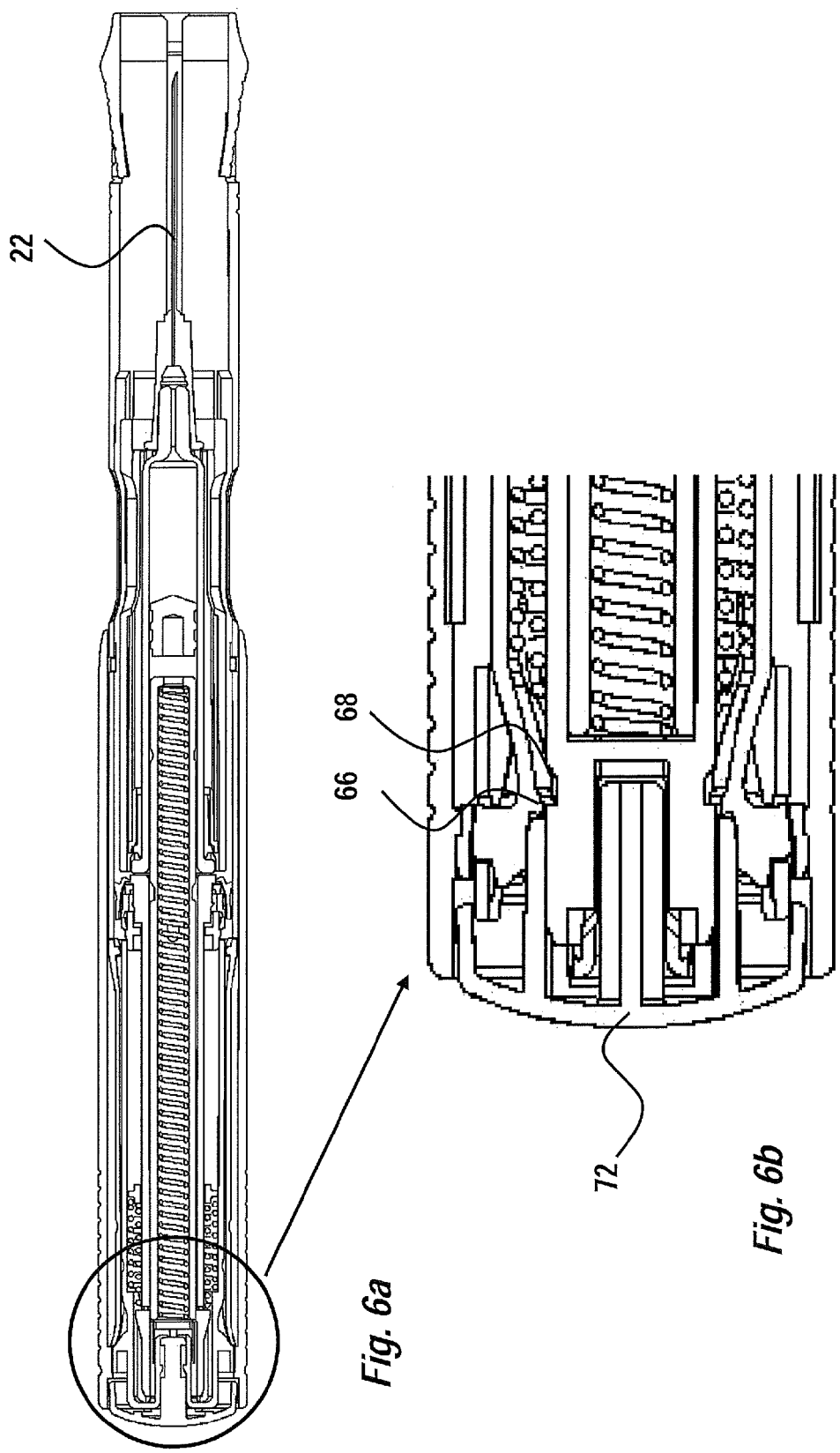

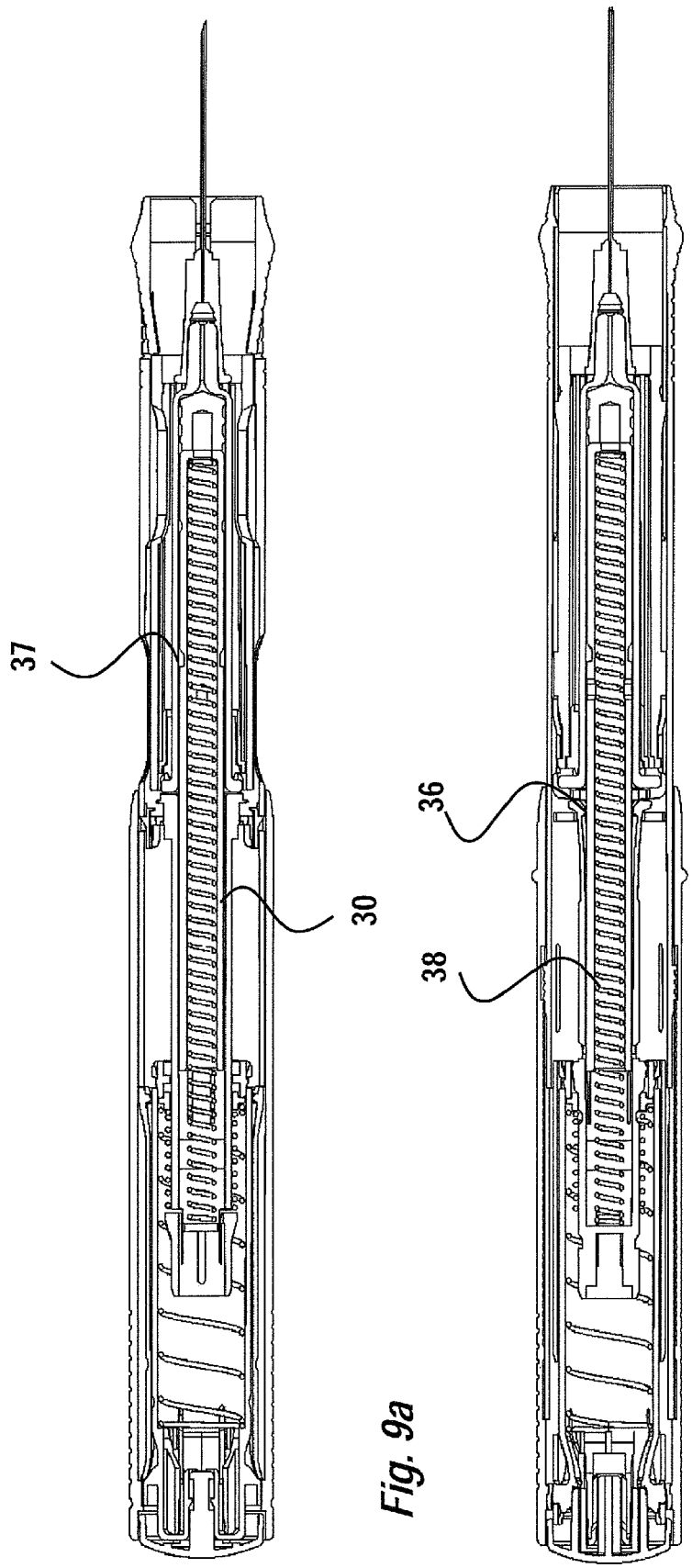

ns, which is relatively simple and of low cost and which overcomes or at least reduces the problems identified above.

AUTOMATIC INJECTION DEVICE WITH ACTIVELY TRIGGERED SYRINGE WITHDRAWAL

TECHNICAL FIELD

The present invention relates to an injector and in particular to an injector having several automatic functions as automatic penetration, automatic injection and automatic active triggering withdrawal.

BACKGROUND

There are many injectors on the market where the aim is to have high degrees of functionality and automatic features, such as in connection with penetration, injection, setting of dose, priming and covering of the needle after use. At the same time there is a demand on robustness, repeatability and reliability regarding the function, which sometimes might be difficult to meet when dealing with complex multi functions involving many interacting components. When there further are demands on low production costs, especially for devices that are to be used only once, the picture becomes even more complex.

There are in the patent literature numerous solutions to injection devices, the bulk of which never enter the market due to that they do not meet the demands in one way or the other. There is therefore a continuous search for solutions that provide the desired functions that at the same time fulfill the functional and/or economical demands.

Many devices having multi-functions that work in sequence, such as for example penetration, followed by injection, followed by withdrawal, have a subsequent sequence triggered at the end of a previous sequence, for example when the needle has reached full penetration depth, the injection sequence is triggered.

Safety margins have been implemented in the devices having multi-functions that work in sequence in order to ensure that each sequence is effective, e.g., in WO-A1-2006057604. Mostly the safety margins are overestimated in the devices, leading to medicament spill after the needle withdrawal, which also results in inaccurate delivered doses.

In EP-A-0 516 473, a retraction mechanism has been proposed wherein, at the point at which a plunger rod reaches the end of a bore in a syringe, a portion of a coupling instantaneously collapses in length as a retraction spring retracts a needle. This proposal suffers the problem that, due to the tolerances of the various components, it cannot be assured that the retraction mechanism will enable retraction of the needle at precisely the moment at which the plunger rod reaches the end of the bore. Therefore, either the mechanism retracts the needle before the plunger rod reaches the end of the bore, such that the syringe is not emptied, or the plunger rod reaches the end of the bore before the mechanism has moved sufficiently far to retract.

Although this problem has been recognized in U.S. Pat. No. 6,159,181 and EP-B1-0 996 473, the proposed solutions have been to provide a user actuated withdrawal mechanism rather than an automatic one and this is considered to be undesirable due to the risk of removing the injector from the injection site before the user actuated withdrawal mechanism has been activated. Then there exists the dangers of having an extended and possibly contaminated needle exposed around the user.

It is an object of the present invention to provide an injection device having an active triggering withdrawal mecha-

SUMMARY

The present invention provides an injector that fulfils the demands that are put on such devices regarding functionality, reliability, and low cost.

In accordance with the invention, an injection device comprises a housing including a container carrier having a medicament container and a needle attached to the medicament container, a needle shield slidable arranged inside said housing with a contact part intended to be applied against an injection site, activation means arranged to be interactively connected to said needle shield and capable of, upon manual activation, initiating a penetration sequence; penetration means interactively connected to said activation means and capable of performing an automatic penetration of the needle, injection means interactively connected to said penetration means and capable of triggering and performing an automatic injection of the medicament, withdrawing means interactively connected to said injection means and capable of triggering and performing an automatic withdrawing of the needle, wherein said device further comprises an active triggering withdrawal mechanism interactively connected to said withdrawing means and capable of allowing said withdrawing means to be triggered when the injection device starts to be removed from the injection site.

The active triggering withdrawal allows the user to have control over when to withdraw the needle, preventing incomplete dosages due to early withdrawal and/or malfunctions in an automatic needle-retraction device.

The injection device is a cost-effective multi-function device that operates with a safe and reliable chain of sequences, thus ensuring that the user receives a proper accurate dose of medicament each time the device is used.

These and other features and advantages of the present invention will become apparent from the following detailed description and the drawings.

BRIEF DESCRIPTION OF THE DRAWINGS

In the following detailed description, reference is made to the drawings, of which.

DETAILED DESCRIPTION

Figure 1:
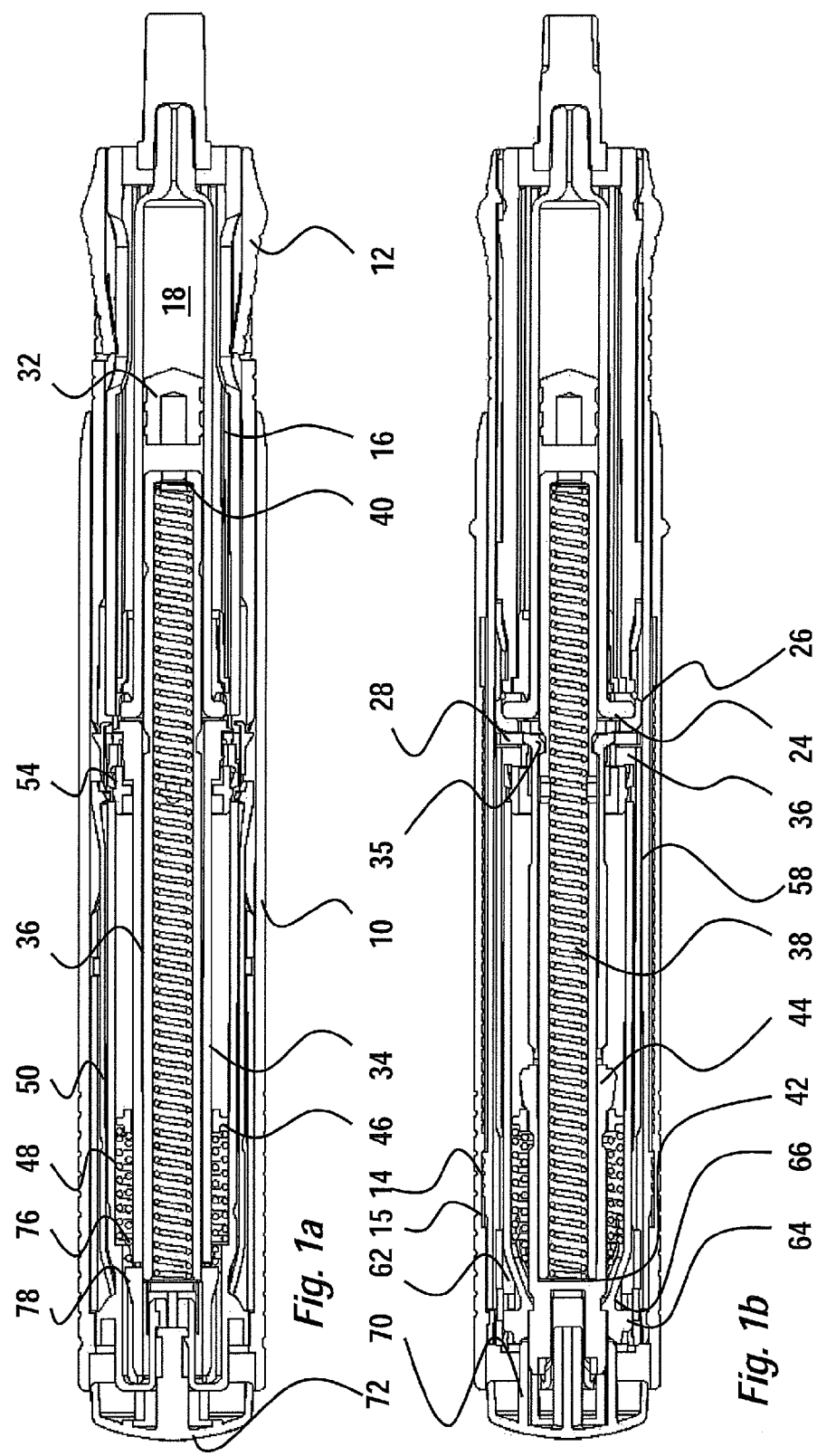
FIG. 1 is a longitudinal cross-section of an embodiment of the present invention.

The device according to the figures comprises a generally tubular housing 10. In the front end of the housing, to the right in FIG. 1, a generally tubular needle shield 12 with a contact part intended to be applied against an injection site is slidable arranged in the housing. When the device is unarmed, the needle shield is held in place by protrusions 14 on its outer surface co-operating with ledges 15 on the inner surface of the housing.

Inside the needle shield in the front area of the device a container carrier 16 is arranged. Inside the container carrier a container 18, containing medicament, is arranged. The container is prevented from moving forward by a circumferential ledge. The front end of the container can be arranged with attachment means for attaching a needle 22 to the container, FIG. 6a. The rear end of the container is seated with a flange 24 adjacent the container carrier 16.

The device comprises activation means arranged to be interactively connected to said needle shield and capable of, upon manual activation, initiating a penetration sequence as it will be explained in detail below. The activation means comprises flexible arms 62 having inwardly extending ledges 66 on a penetration sleeve 50, recesses 60 on the lock-out sleeve 58, a circumferential groove 68 on an activation housing 34, and an activation button 72 having inwardly extending parts 74 facing the arms 62.

Further, the device comprises penetration means interactively connected to the activation means and capable of performing an automatic penetration of the needle as it will be explained in detail below. The penetration means comprises tongues 26 arranged on an activation housing 34 and snap-fitted to the container carrier 16, outwardly extending protrusions arranged on flexible arms 44 which are arranged on said activation housing; a retraction release ring 46 abutting said outwardly extending protrusions, and a penetration spring 48 arranged between the retraction release ring 46 and an inner rear wall of a penetration sleeve 50.

The device also comprises injection means interactively connected to the penetration means and capable of triggering and performing an automatic injection of the medicament as it will be explained in detail below. The injection means comprises flexible tongues 36 arranged on the activation housing 34 and where each tongue is arranged with inwardly directed ledges 35; a plunger rod 30 having a circumferential groove 37 where the ledges 35 are positioned when the device is unarmed; and an injection spring 38 arranged between a front wall 40 of the plunger rod and a rear wall 42 of the activation housing.

Further, the device comprises withdrawing means interactively connected to the injection means and capable of triggering and performing an automatic withdrawing the needle as it will be explained in detail below. The withdrawing means comprises a penetration retraction spring 76 arranged between the retraction release ring 46 and protrusions 78 arranged on an activation housing 34; and the flexible arms 44 arranged on said activation housing.

The plunger rod 30 extends into the container with one end adjacent a stopper 32 arranged within the container. The rear end of the plunger rod is surrounded by the activation housing 34 which is snap-fitted to the container carrier 16 by tongues 26 of said activation housing. The activation housing is arranged with flexible tongues 36, where each tongue is arranged with inwardly directed ledges 35. In the initial state, these ledges are positioned in a circumferential groove 37 on the plunger rod 30. The tongues and ledges are held in this position by the injection release ring 28.

Inside the plunger rod, the injection spring 38 is arranged compressed between a front wall 40 of the plunger rod 30 and a rear wall of the activation housing 34. The activation housing is further arranged with outwardly extending protrusions arranged on flexible arms 44. Abutting the protrusions is the retraction release ring 46, which will be described in more detail below.

The penetration spring 48, is arranged between the retraction release ring 46 and an inner rear wall of the penetration sleeve 50. At the front end of the penetration sleeve, a retraction spring retainer 52 is snap fitted with the penetration sleeve 50 by outwardly directed protrusions 54 having a straight part and a ramped part, extending into recesses 56 of the penetration sleeve. Outside the penetration sleeve is arranged the lockout sleeve 58. At the rear part of the lockout sleeve 58, tongues with recesses 60 are arranged adjacent flexible arms 62 of the penetration sleeve, which arms are arranged with outwardly extending protrusions 64 as well as inwardly extending ledges 66. In the initial position these ledges are in contact with a wall of a circumferential groove 68 on the activation housing 34. The upper part of the arms is further arranged with inclined surfaces 70.

Figure 2:
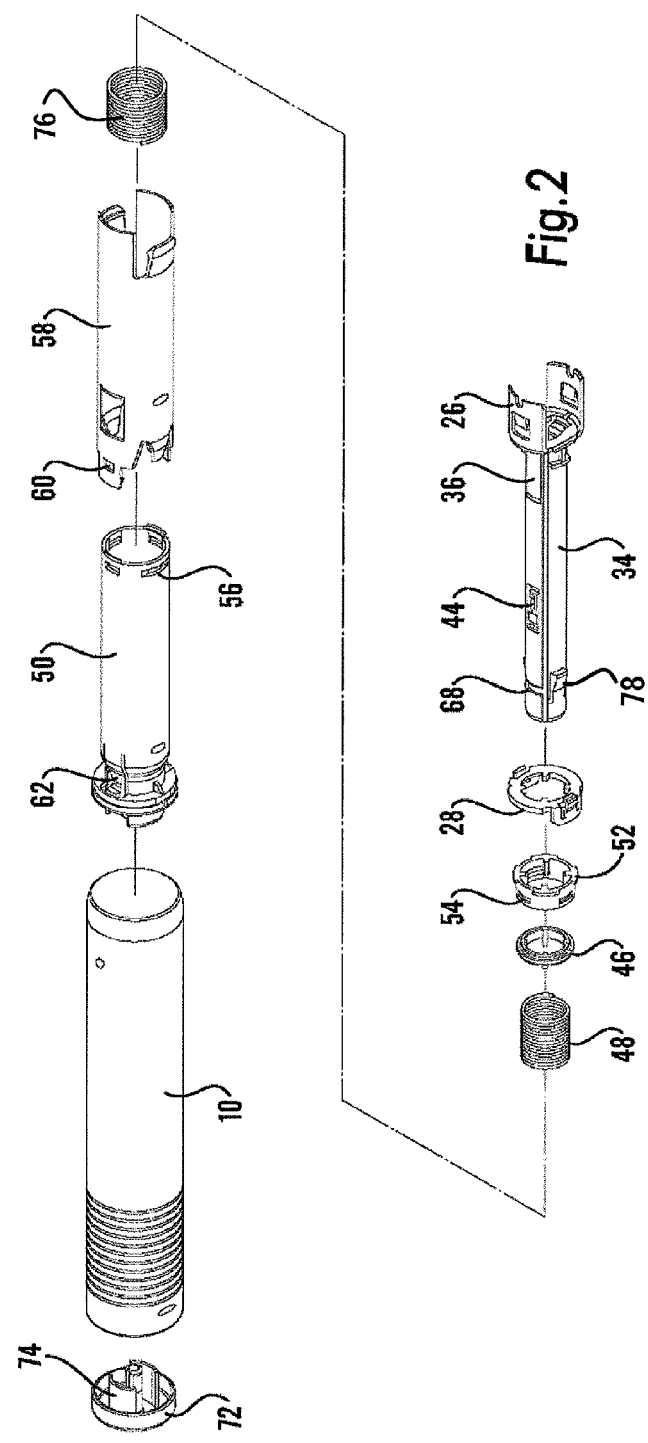
FIGS. 2-3 are exploded views of the injector of FIG. 1, FIGS. 4-11 show different functional steps of the device of FIG. 1, FIG. 12a, b show detailed views of a second embodiment of the present invention.
Figure 3:
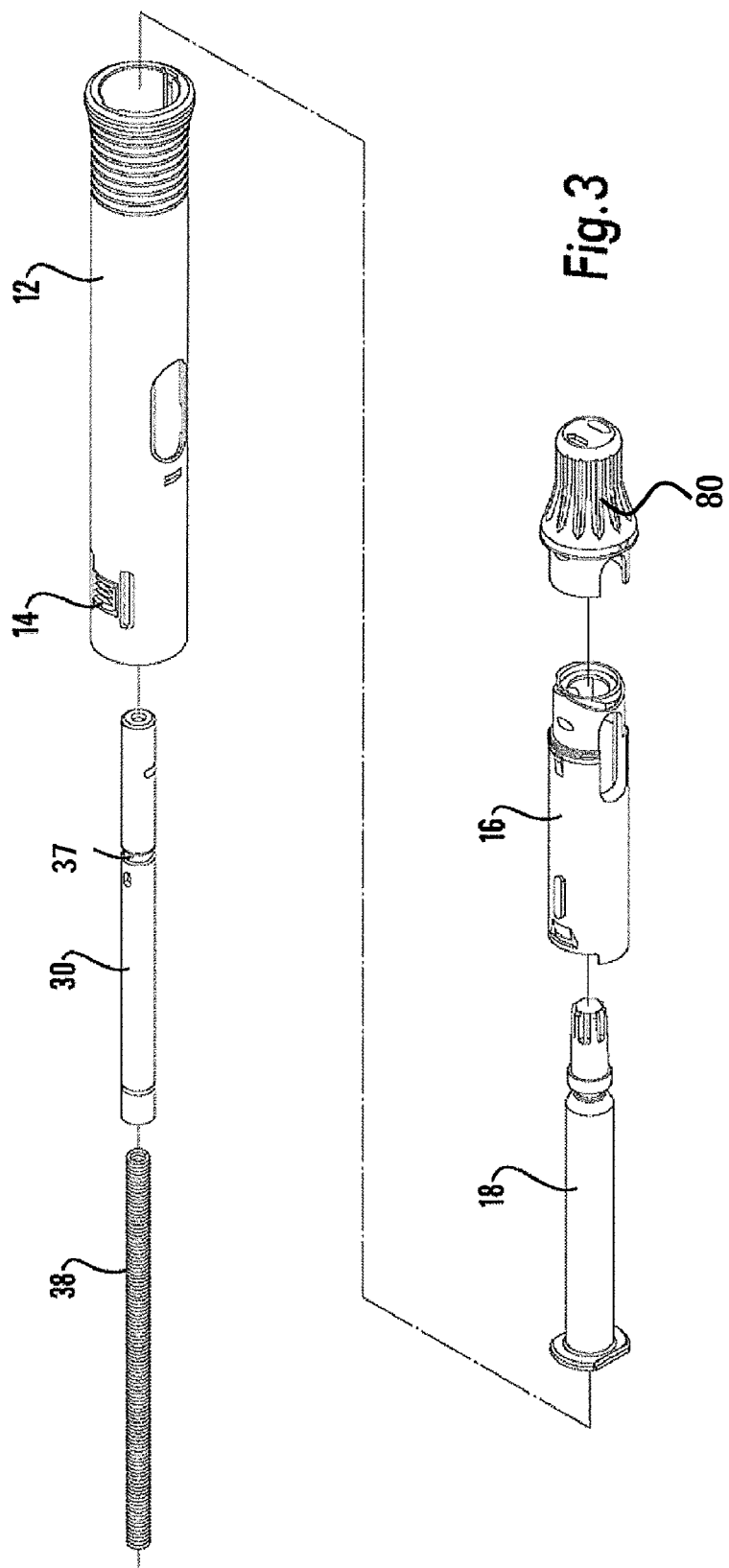

At the upper end of the housing an activation button 72 is slidably arranged, having inwardly extending parts 74, which are arranged with inclined surfaces facing the inclined surfaces 70 of the arms 62. Since the tongues with recesses 60 are arranged adjacent the flexible arms 62, the arms 62 cannot be moved radially outwards and consequently blocks the activation button to be moved. Further a penetration retraction spring 76 is arranged between the retraction release ring 46 and protrusions 78 arranged on the activation housing 34, FIG. 2.

Figure 4:
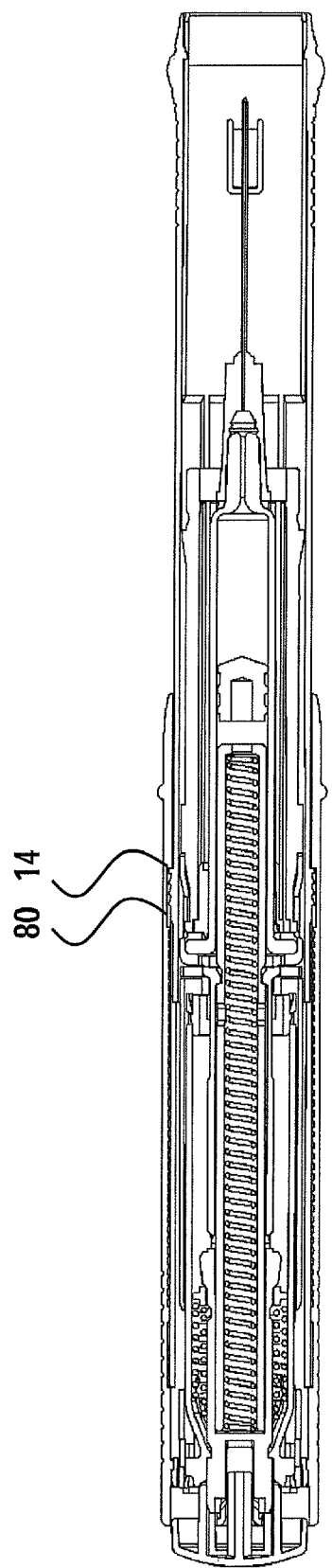

The device is intended to function as follows. In the initial position or when the device is unarmed, the needle shield 12 is positioned inside the housing 10 and held in place by the protrusions 14 acting against the ledge of the housing, FIG. 1. The device may be delivered with a protective cap 80 inserted into the front end of the needle shield surrounding the front end of the container 18 with its syringe cap. The protective cap is removed, whereby the syringe cap is also removed, and a needle 22 is attached to the container. The needle shield 12 is then pushed manually forward until the protrusions 14 of the needle shield enter a recess 82 on the inner surface of the housing 10 for arming the injection device, FIG. 4a. The protrusions have such a configuration that they are able to slide over the ledge when the needle shield is extended but prevent a pushing in of the needle shield when they have entered the recess. When in the outermost position, the needle shield is connected to the lock-out sleeve by snap-in members connecting to cut-outs (not shown). The needle shield is now movably connected to the lock-out sleeve 58.

The device is now ready to use. In order to initiate a penetration sequence, the user places the front end of the needle shield 12 against an injection site wherein the pressing of the needle shield 12 causes it to move a short distance inwards until the protrusions 14 of the needle shield abut the upper wall of the recess 80, FIG. 5a. This movement causes the lockout sleeve 58 to be moved the same short distance because of the connection between the needle shield 12 and the lockout sleeve 58.

If the device is lifted or removed from the injection site the lockout sleeve and the needle shield are resiliently moved back to the initial position due to the interaction between the tongues of the lock out sleeve 58 and inclined surfaces of the penetration sleeve 50.

The movement of the lockout sleeve causes the recesses 60 to be positioned outside of the outwardly extending protrusions 64 of the arms 62 of the penetration sleeve 50, FIG. 5b, which enables the button 72 to be depressed whereby the inclined surfaces of the inwardly extending parts act on the inclined surfaces 70 of the arms 62, causing them to move radially outwards. This is not possible when the lockout sleeve 58 has not been moved since the protrusions of the arms then abut the inner surface of the lockout sleeve.

Figures 7A, 7B:
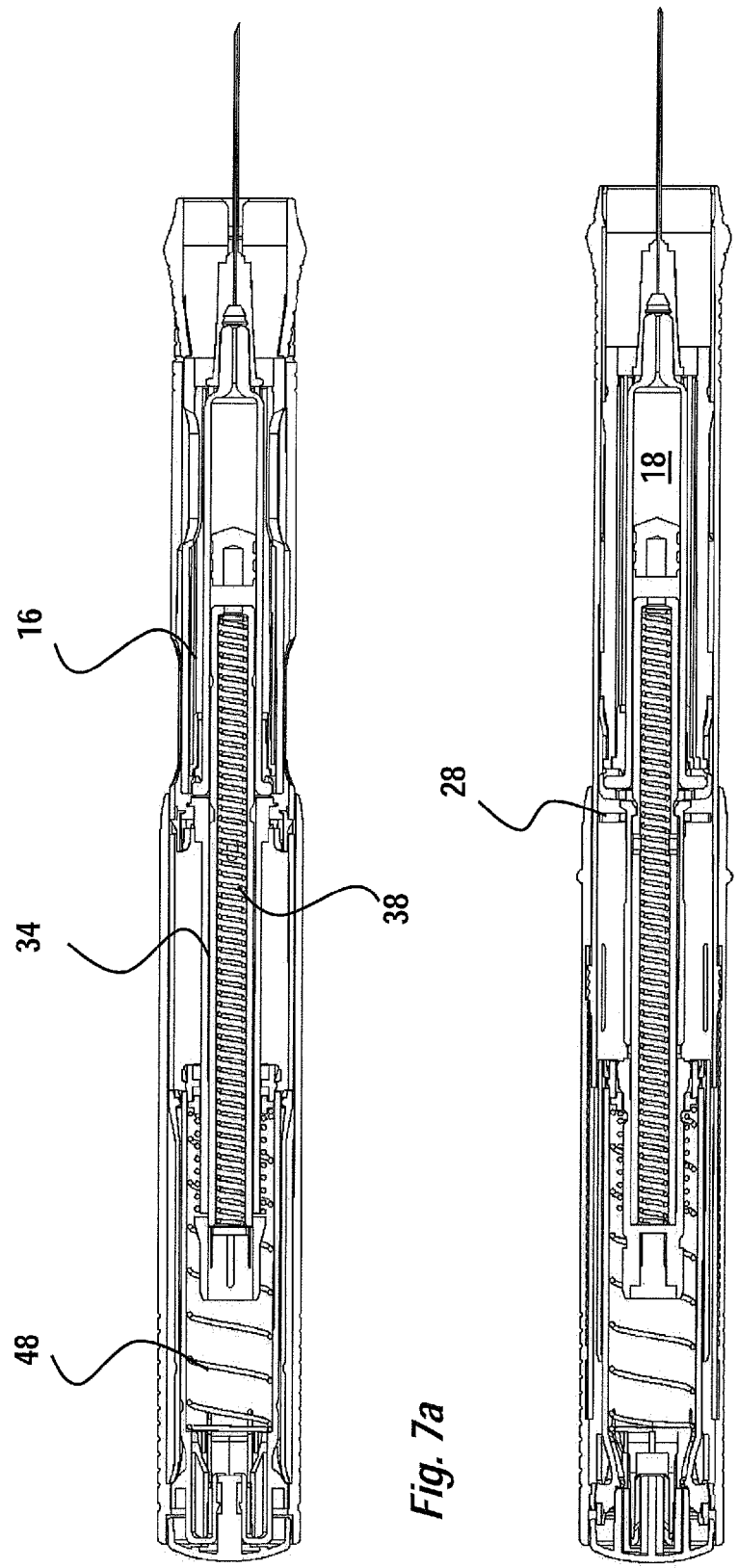

When the arms move radially outwards, the inwardly directed ledges 66 of the arms 62 are moved out of contact with the circumferential groove 68 of the activation housing 34, FIG. 6b, which then is moved forward by the penetration spring 48 acting on the retraction release ring 46 which is held in place relative the activation housing 34 by the protrusions of the flexible arms 44, FIG. 7. Thus both the activation housing 34, the plunger rod 30 arranged inside the activation housing, the container carrier 16 connected to the activation housing, the injection release ring 28 and the syringe 18 are moved forward causing a penetration of the needle into the injection site.

At a certain depth the injection release ring 28 is stopped by the engagement of protrusions on its flexible arms into slots on the shield, which frees the flexible tongues 36 because they pass the ring due to the continued movement of the activation housing 34. The freeing of the tongues cause them to flex outwards radially and lock in pockets, whereby the inwardly directed ledges are moved out of contact with the groove 38 on the plunger rod 30 and the movement of the activation housing 34, and thus the penetration, is stopped when the front end of the container carrier 16 abuts tongues 92 of the needle shield, FIG. 8.

The releasing of the inwardly directed ledges from the groove 38 on the plunger rod 30 triggers an injection by releasing the plunger rod due to the force of the injection spring 38, whereby it pushes on the stopper 32 and an injection is performed, FIG. 9. When the injection has been completed and/or an indication has been given to the user as e.g. a sound or the active looking at a window showing that the injection has been completed; the user removes the device from the injection site by lifting the injection device up and away from the injection site, hereafter called an active triggering withdrawal.

Figure 8A:
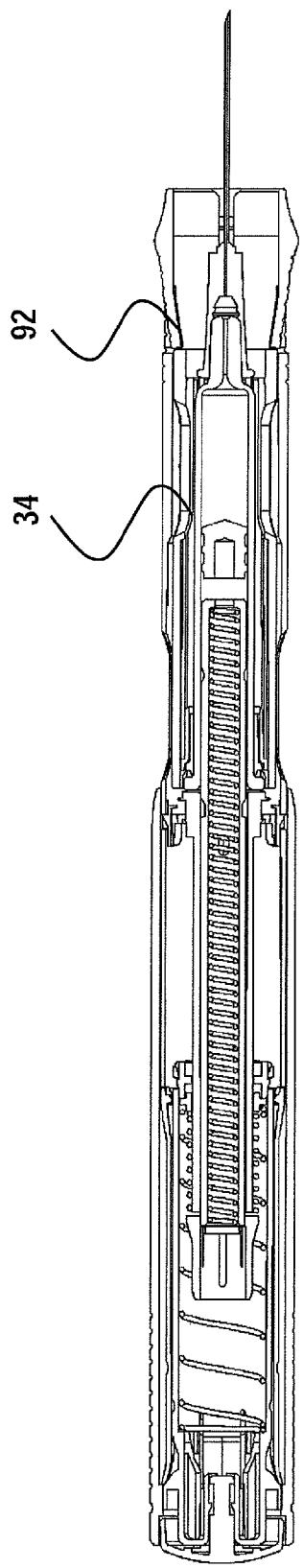
Figure 8B:
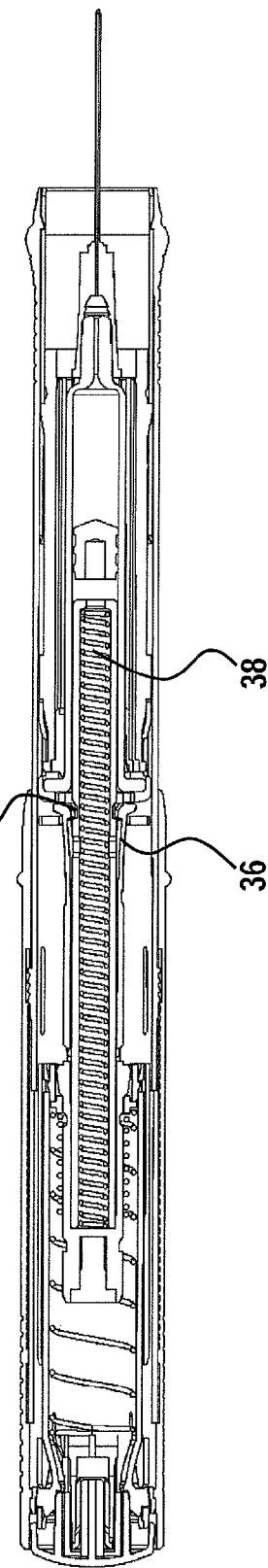
Figures 10A, 10B:
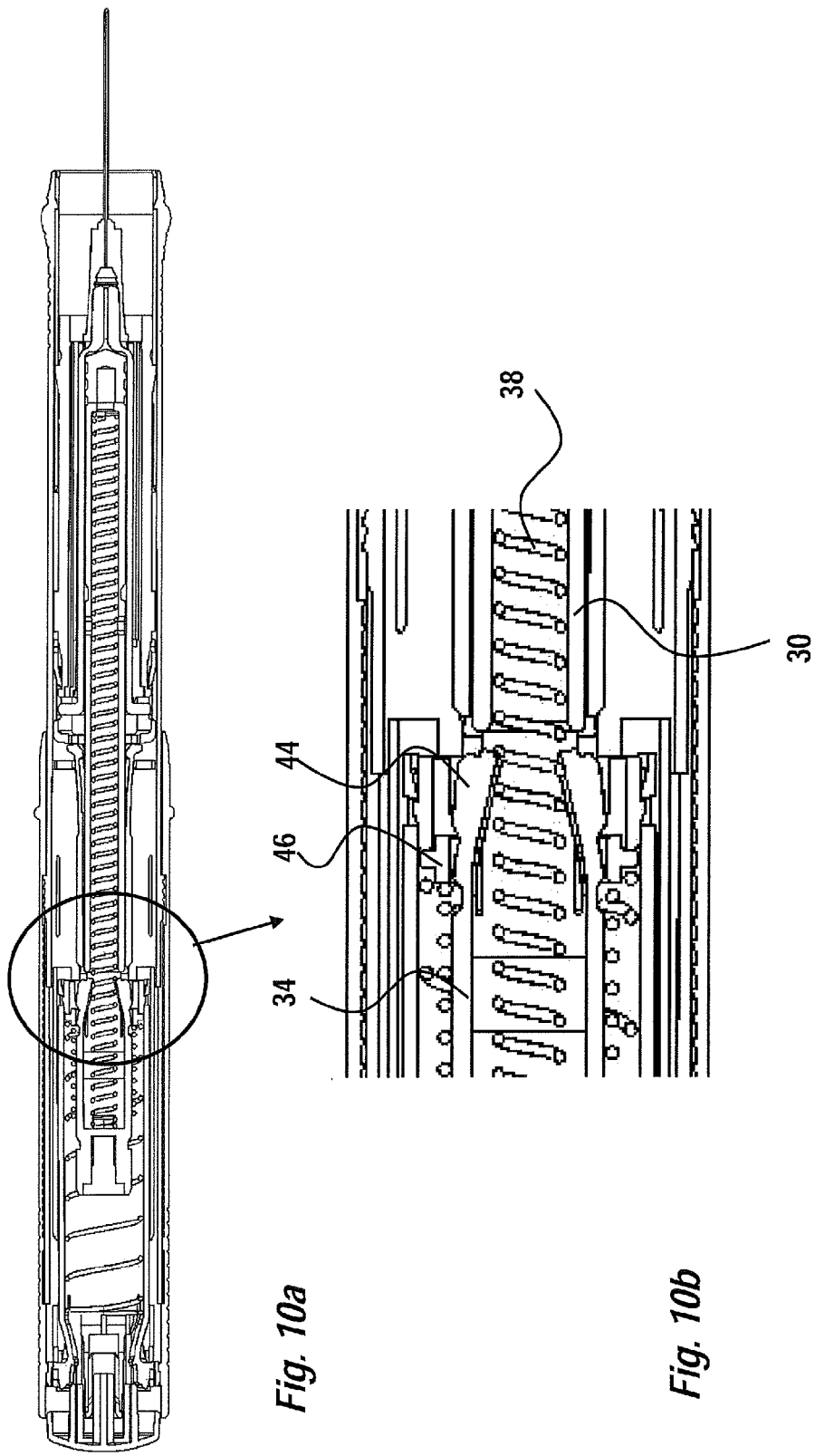
Figure 11A:
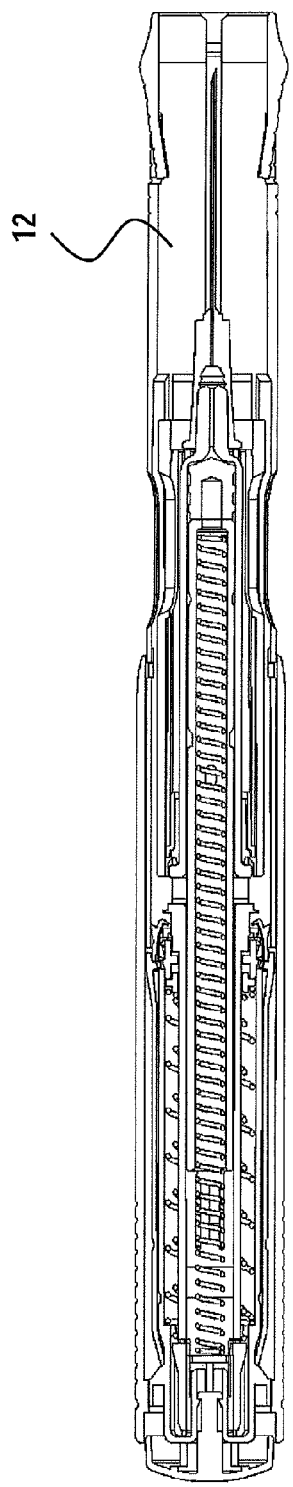
Figure 11B:
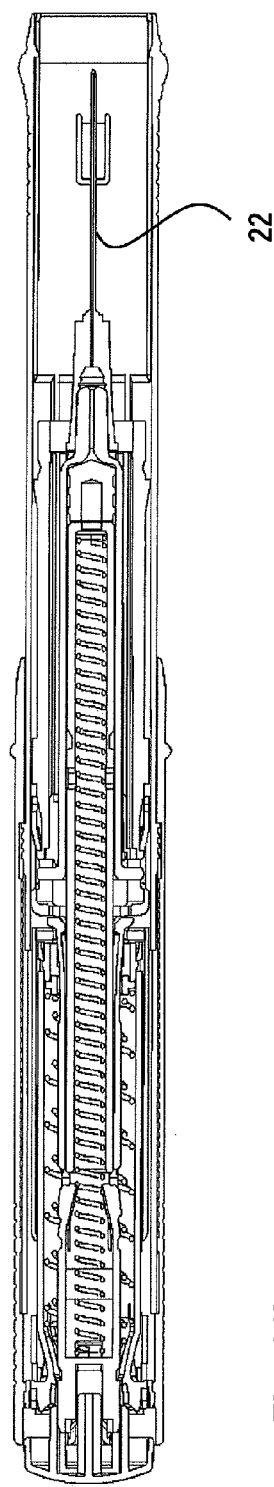
Figure 12A:
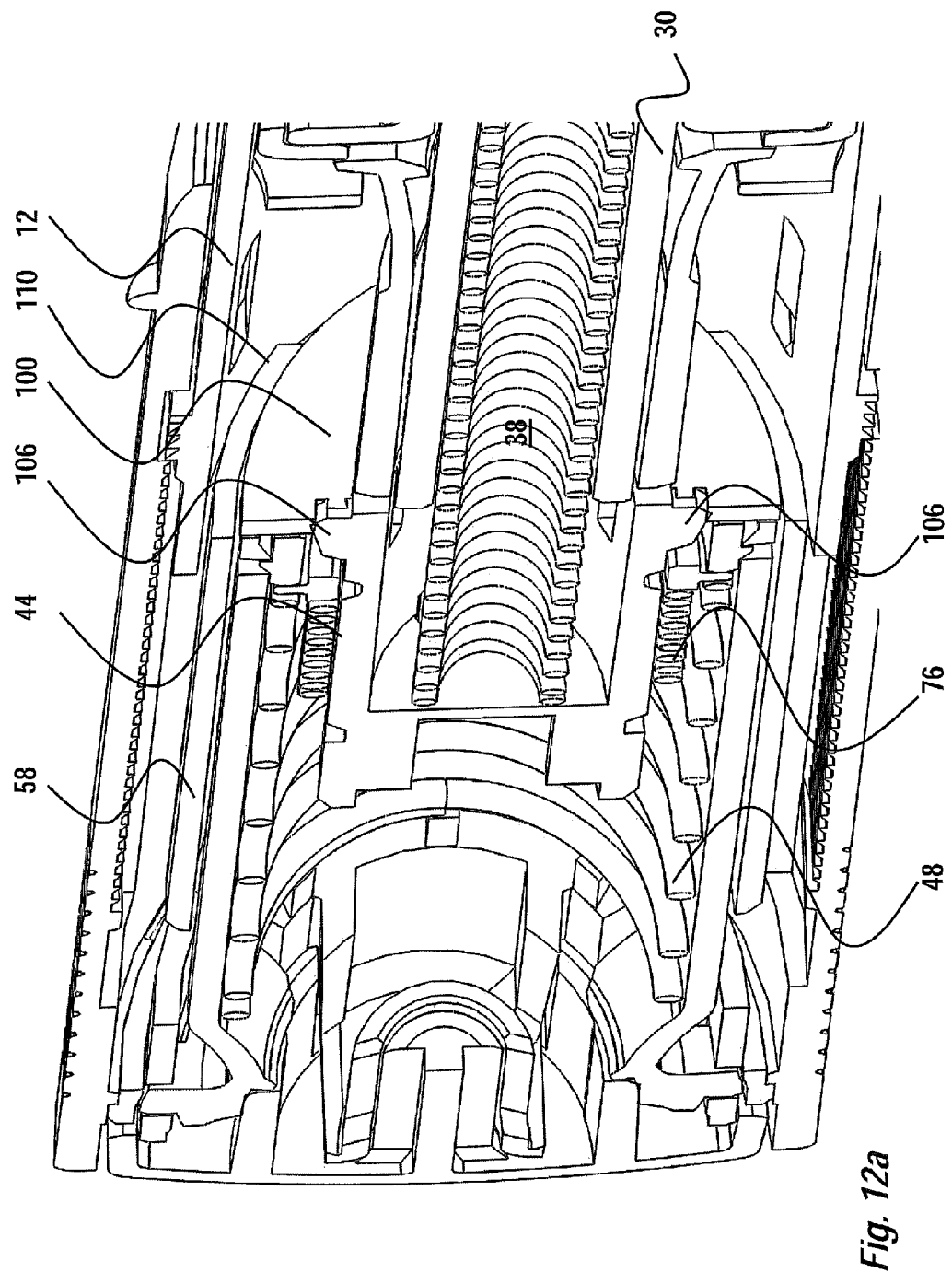
Figure 12B:
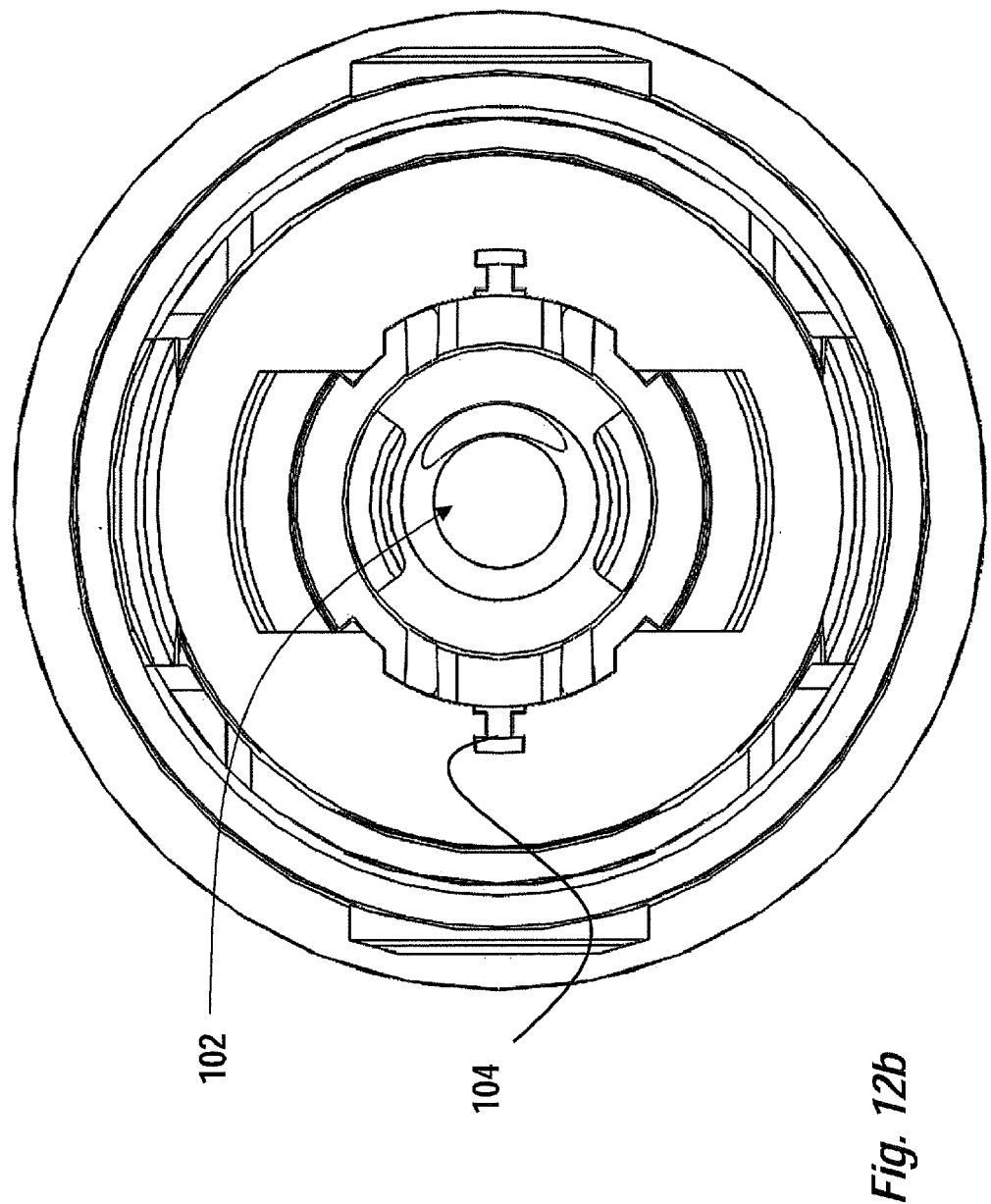
Figure 13A:
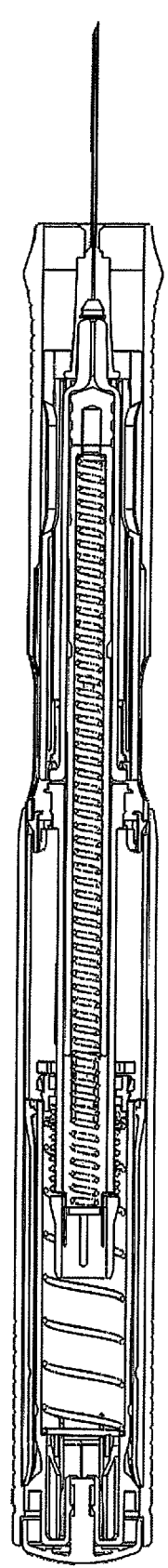
FIG. 13-15 show different functional steps of the device of FIG. 12.
Figure 13B:
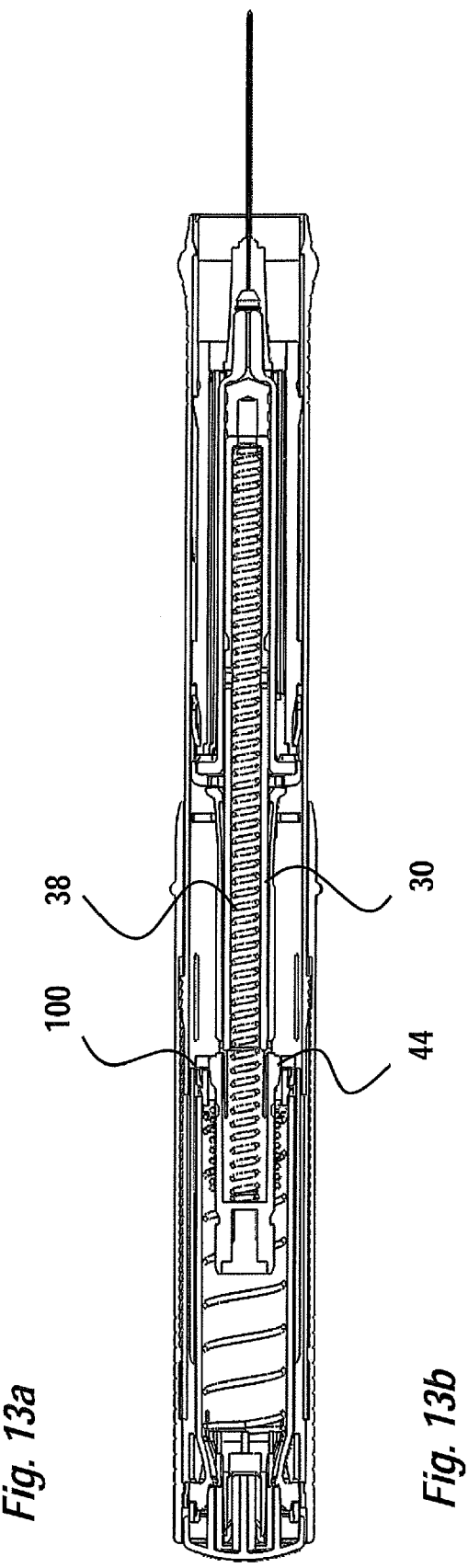
Figure 14A:
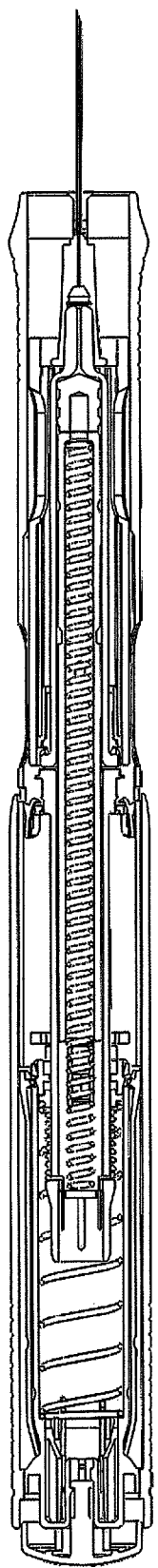
Figure 14B:
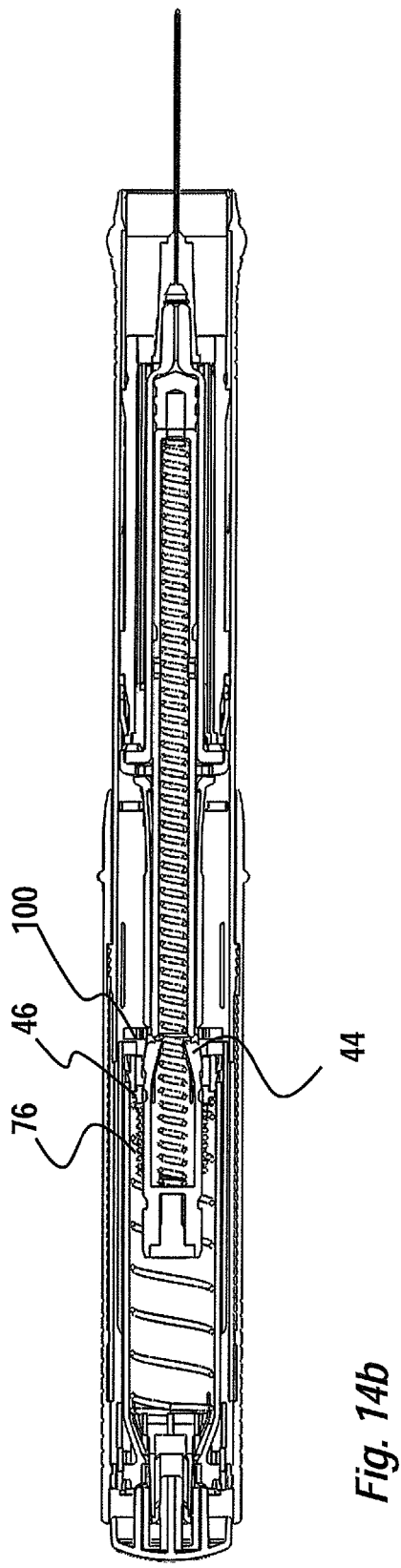
Figure 15A:
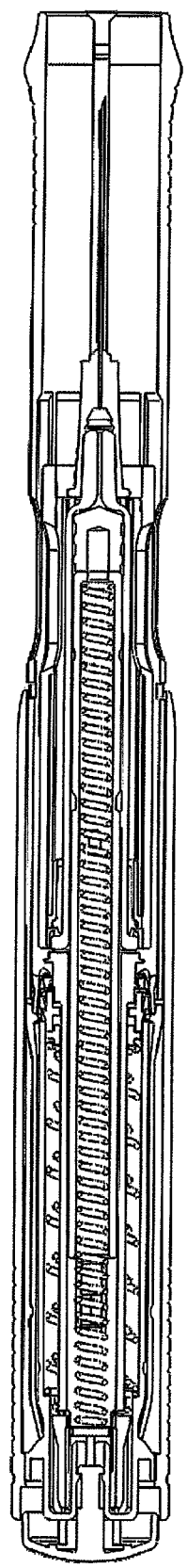
Figure 15B:
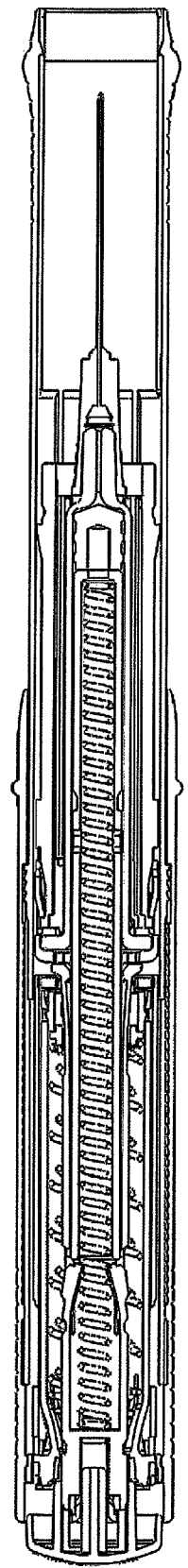

The active triggering withdrawal is performed by an active triggering withdrawal mechanism which comprises means as tongues 92 arranged on the inner surface of the needle shield, FIG. 8a; and the penetration spring 48. Said penetration spring 48 is used for urging the medicament container carrier with the container and needle forward during the penetration sequence until the front edge of the container carrier 16 contacts the tongues 92. When the injector is lifted or removed from the injection site, the penetration spring 48 causes the container carrier 16 and thus the needle shield 12, because of the above mentioned connection, to move forward a certain distance. The forward movement of the container carrier also causes the plunger rod 30 to move forward in relation to the activation housing 34. The upper edge of the plunger rod will then pass the outwardly directed protrusions of the flexible arms 44 holding the retraction release ring, FIG. 10. This will in turn allow said flexible arms 44 to move inwards, which in turn frees the retraction release ring 46 and thereby triggering the withdrawal sequence. The retraction spring 76 is now free to expand whereby the container carrier together with the injection needle is drawn into the housing of the injector by the force of the retraction spring 76 acting on the protrusions 78 of the activation housing 34. The needle is now protected inside the needle shield 12, FIG. 11.

FIGS. 12-15 disclose a second embodiment of the present invention where the same components as for the previous embodiment have the same reference numerals. Further, this embodiment has the same components and function regarding penetration and injection and these steps will therefore not be described in detail. The active triggering withdrawal mechanism comprises in this embodiment means as grooves 104 of e.g. a lock plate 100 surrounding the activation housing 34. The grooves 104 have a certain shape such that they are adapted to cooperate with corresponding ledges 106 of the protrusions of the flexible arms 44.

This embodiment is intended to function as follows. The penetration and injection are performed in the same manner as described above. However, when the penetration spring 48 urges the activation housing, the medicament container carrier with the container and the needle forward during the penetration sequence; the ledges 106 comes into engagement with the grooves 104 for preventing the flexible arms 44 from being moved inwards FIGS. 12 and 13. Further, when the injector is removed or lifted from the injection site, the lock-out sleeve 58 and thus the needle shield are moved forward a certain distance due to the interaction between the tongues of the lock out sleeve 58 and inclined surfaces of the penetration sleeve 50. The front surface 110 of the lock-out sleeve 58 comes in contact with the lock plate and the movement causes the lock plate to move forward such that the ledges 106 comes out of contact with the grooves 104, FIG. 14. This in turn enables the flexible arms 44 to collapsing inwards.

The collapsing causes the retraction release ring 46 to pass the protrusions of the flexible arms 44 triggering the withdrawing of the needle, and the container carrier together with the injection needle is drawn into the housing of the injector by the force of the retraction spring 76 acting on the protrusions 78 of the activation housing 34. The needle is now protected inside the needle shield 12.

It will be understood that the embodiments described above and shown in the drawings are to be regarded only as non-limiting examples of the invention and that they may be modified within the scope of the patent claims.

The invention claimed is:
1. An injection device, comprising:
a housing, including a container carrier having a medicament container and a needle attached to the medicament container;
a needle shield slidably arranged inside the housing with a contact part configured for application against an injection site;
an activation mechanism interactively connected to the needle shield and configured, upon manual activation, for initiating a penetration sequence, wherein the activation mechanism comprises first flexible arms having inwardly extending ledges on a penetration sleeve, recesses on a lock-out sleeve, a circumferential groove on an activation housing, and an activation button having inwardly extending parts facing the first flexible arms;
a penetration mechanism interactively connected to the activation mechanism and configured for performing an automatic penetration of the needle, wherein the penetration mechanism comprises tongues arranged on the activation housing and snap-fitted to the container carrier, outwardly extending protrusions arranged on second flexible arms on the activation housing, a retraction release ring abutting the outwardly extending protrusions, and a penetration spring arranged between the retraction release ring and an inner rear wall of the penetration sleeve;
an injection mechanism interactively connected to the penetration mechanism and configured for triggering and performing an automatic injection of the medicament, wherein the injection mechanism comprises flexible tongues arranged on the activation housing, each tongue having inwardly directed ledges, a plunger rod having a circumferential groove where the inwardly directed ledges are positioned when the device is unarmed, and an injection spring arranged between a front wall of the plunger rod and a rear wall of the activation housing;
a withdrawal mechanism interactively connected to the injection mechanism and configured for triggering and performing an automatic withdrawal of the needle, wherein the withdrawal mechanism comprises a penetration retraction spring arranged between the retrac- tion release ring and protrusions arranged on the activation housing and the second flexible arms on the activation housing; and an active triggering withdrawal mechanism interactively connected to the withdrawal mechanism and configured for allowing the withdrawal mechanism to be triggered when the injection device starts to be removed from the injection site, wherein the active triggering withdrawal mechanism comprises grooves arranged on a lock plate surrounding the activation housing, and corresponding ledges arranged on the protrusions of the second flexible arms, such that when the penetration spring urges the activation housing and the container carrier forward, the ledges engage the grooves for preventing the second flexible arms from being moved inward;

wherein when the injection device is removed or lifted from the injection site, a front surface of the lock-out sleeve causes the lock plate to move forward so that the ledges come out of contact with the grooves, enabling the flexible arms to collapse inward, allowing the retraction release ring to pass the protrusions of the second flexible arms, such that the container carrier is drawn into the housing by the force of the retraction spring acting on the protrusions.

2. The injection device of claim 1, wherein the needle shield is initially held inside the housing when the device is unarmed.

3. The injection device of claim 2, wherein the needle shield is arranged to be manually pulled such that protrusions of the needle shield enter a recess on an inner surface of the housing for arming the injection device and is connected to the lock-out sleeve by snap-in members.

4. The injection device of claim 3, wherein the ledges contact a wall of the circumferential groove, and the recesses are arranged adjacent the first flexible arms blocking movement of the activation button when the device is unarmed.

5. The injection device of claim 4, wherein the lock-out sleeve and the needle shield are arranged to be resiliently moved due to interaction between the tongues of the lock sleeve and inclined surfaces of the penetration sleeve, when the injection device is lifted or removed from the injection site.

* * * * *